US005593422A

United States Patent [19]

Muijs Van de Moer et al.

[11] Patent Number: 5,593,422
[45] Date of Patent: Jan. 14, 1997

[54] OCCLUSION ASSEMBLY FOR SEALING OPENINGS IN BLOOD VESSELS AND A METHOD FOR SEALING OPENINGS IN BLOOD VESSELS

[76] Inventors: Wouter M. Muijs Van de Moer, Grindweg 56, 3055 VB Rotterdam; Rienk Rienks, Mennestraat 17, 3882 AN Putten, both of Netherlands

[21] Appl. No.: 369,588

[22] Filed: Jan. 6, 1995

Related U.S. Application Data

[63] Continuation of Ser. No. 248,571, Mar. 24, 1994, abandoned, which is a continuation of Ser. No. 776,281, filed as PCT/NL90/00078, May 29, 1989, published as WO90/14796, Dec. 13, 1990, abandoned.

[30] Foreign Application Priority Data

May 29, 1989 [NL] Netherlands ............... 8901350

[51] Int. Cl.$^6$ .................................................. A61B 17/00
[52] U.S. Cl. .................. 606/213; 606/215; 606/232; 604/288; 604/285
[58] Field of Search .................... 606/213, 215, 606/158, 157, 151, 232; 604/167, 169, 285, 288; 623/11; 128/898, 899

[56] References Cited

U.S. PATENT DOCUMENTS

| | | | |
|---|---|---|---|
| 3,874,388 | 4/1975 | King et al. | 606/232 |
| 4,007,743 | 2/1977 | Blake | 623/11 |
| 4,519,392 | 5/1985 | Lingua | 606/157 |
| 4,669,473 | 6/1987 | Richards et al. | 606/215 |
| 4,750,492 | 6/1988 | Jacobs | 606/232 |
| 4,852,568 | 8/1989 | Kensey | 606/213 |
| 4,917,089 | 4/1990 | Sideris | 128/899 |
| 4,925,664 | 5/1990 | Jackson et al. | 424/537 |
| 4,931,464 | 6/1990 | Grover et al. | 514/423 |
| 5,021,059 | 6/1991 | Kensey et al. | 606/213 |
| 5,053,046 | 10/1991 | Janese | 606/213 |
| 5,192,302 | 3/1993 | Kensey et al. . | |
| 5,222,974 | 6/1993 | Kensey et al. . | |
| 5,275,616 | 1/1994 | Fowler . | |
| 5,282,827 | 2/1994 | Kensey et al. . | |
| 5,306,254 | 4/1994 | Nash et al. . | |
| 5,330,445 | 7/1994 | Haaga . | |
| 5,342,393 | 8/1994 | Stack . | |
| 5,350,399 | 9/1994 | Erlebacher et al. . | |
| 5,354,271 | 10/1994 | Voda . | |

FOREIGN PATENT DOCUMENTS 482350 4/1992 European Pat. Off. .

*Primary Examiner*—Michael Powell Buiz
*Assistant Examiner*—Jeffrey A. Schmidt

[57] ABSTRACT

Occlusion assembly for sealing openings in blood vessels, consisting of an occlusion element and fixing element to be fitted through the openings in the blood vessel. The fixing element is firmly connected to a retaining element. A locking element engages on the retaining element. This locking element is fitted horizontally against the outside of the blood vessel.

68 Claims, 3 Drawing Sheets

OCCLUSION ASSEMBLY FOR SEALING OPENINGS IN BLOOD VESSELS AND A METHOD FOR SEALING OPENINGS IN BLOOD VESSELS

This is a continuation of applications Ser. No. 08/248,571 now abandoned filed on Mar. 24, 1994 which is a continuation of 07/776,281 filed Nov. 21, 1991 now abandoned. International Application PCT/NL90/00078 filed on May 29, 1989, and published as WO90/14796 on Dec. 13, 1990 and which designated the U.S.

The invention relates to an occlusion assembly for sealing openings in blood vessels, comprising a spreadable occlusion element which is to be fitted through the opening in the blood vessel and on which a flexible retaining element passing through the wall of the blood vessel engages, a locking element engaging on the retaining element.

An occlusion assembly of this type is disclosed in U.S. Pat. No. 4,744,364. In this patent it is stated that there is a possibility for sliding a locking element over the retaining element, said locking element then lying against the skin of the user. That is to say, the force necessary to hold the occlusion element against the wall of the blood vessel is led by the retaining element through the outside of the wall of the blood vessel through the skin to the outside of the skin.

With this arrangement, as already indicated, the occlusion element is located on the inside of the blood vessel. This occlusion element is in general a material which dissolves in time, so that after a few weeks the opening in the wall of the blood vessel is sealed and no further traces of the occlusion element are found. Because the retaining element extends both through the wall of the blood vessel and the adjacent skin, it is very difficult to apply a controlled tension thereto. After all, it is highly conceivable that movement takes place between the blood vessel and the skin, which will result in an uncontrolled high or low tension. In practice, however, it has been found that it is necessary to apply some tension to the retaining element in order to press the occlusion element in a guaranteed manner against the wall of the blood vessel. If this tension is inadequate or is not present, there is a risk that the occlusion element no longer performs its function well, with the possible complication that the occlusion element no longer completely seals the openings, as a result of which very serious consequences can arise. If the tension is too high, there is a risk of rupture or of the occlusion element being pulled through the opening in the blood vessel. This means that the occlusion assembly according to U.S. Pat. No. 4,744,364 is either not admissible or is admissible only in situations where it can be guaranteed that there will be no mutual movement between the wall of the blood vessel and the skin during the first few days, that is to say that the patient must remain immobile.

The aim of the present invention is to overcome this disadvantage and to provide an occlusion assembly with which it is possible to apply more tension to the retaining element.

This aim is achieved with an occlusion assembly as described above, in that the occlusion assembly comprises a fixing element, firmly connected to the retaining element, and with which the position of the fixing element on the retaining element is such that, in use, the fixing element lies in the blood vessel against the non-occluding side of the occlusion element. In contrast to the locking element according to the U.S. specification, the locking element according to the present invention is fitted so that it lies horizontally against the wall of the blood vessel. By this means problems relating to mutual shifting of the wall of the blood vessel and the skin, with resultant tension concentrations on the retaining element, are avoided. Because it is now possible to apply greater tension to the retaining element, it can be guaranteed that the occlusion element remains in its place. In practice it has been found that there is then a risk that the occlusion element is pulled through the opening in the wall of the blood vessel. In order to avoid this, the fixing element is fitted.

According to a preferred embodiment of the invention, the fixing element is a curved-plated rod-shaped element and the retaining element is fitted in the centre thereof in such a way that when a force is applied the centre of the rod-shaped element touches the occlusion element first. In this way an even force distribution over the occlusion element is provided.

According to a further advantageous embodiment of the invention, the locking element is to be fitted movably over the retaining element against the outside of the blood vessel.

According to a further advantageous embodiment, at least one of the occlusion element or the elements is made from bioabsorbable material. Consequently this part will disappear in time without leaving any trace. According to an advantageous embodiment, the bioabsorbable material comprises collagen or alginate. According to an advantageous embodiment, the occlusion element is in sheet form and essentially circular, heart-shaped or oval. According to a further advantageous embodiment, the occlusion element contains agents which combat stenosis, such as angiotensin II-converting enzyme inhibitor.

The invention also relates to a method for fitting an occlusion assembly in an opening in a blood vessel, comprising the positioning of a sheath through the opening in the blood vessel, guiding an occlusion element and a retaining element, which is coupled therewith, through said sheath into the blood vessel, removing the sheath from the opening in the blood vessel and then placing a locking element on the retaining element. A method of this type is disclosed in U.S. Pat. No. 4,744,364. As already indicated above, with this method the locking element is placed horizontally against the skin. It has likewise been stated that this has the disadvantage that it is not possible with this arrangement to guarantee that the tension on the retaining element with which the occlusion element is pressed against the wall of the blood vessel is always sufficient.

The aim of the present method is to provide means of overcoming this disadvantage. This aim is achieved in that the locking element is fitted horizontally against the outside of the blood vessel. By this means effects of mutual movement between the wall of the blood vessel and the skin and any living tissue between the two are avoided. According to an advantageous embodiment of this method, the retaining element is connected to a fixing element, which is inserted in the sheath before the occlusion element.

The invention is illustrated in more detail below with reference to the illustrative embodiments shown in the drawing. In the drawing.

Figure 5A:
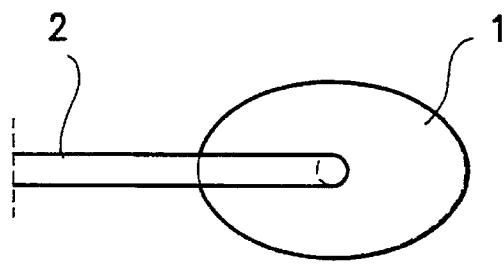
Figure 5B:
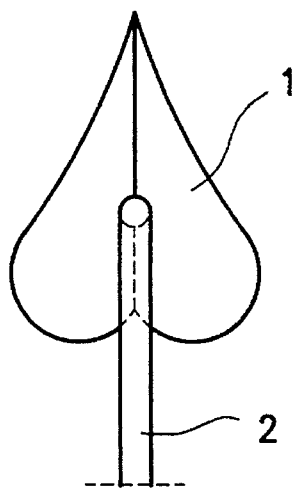
Figure 5C:
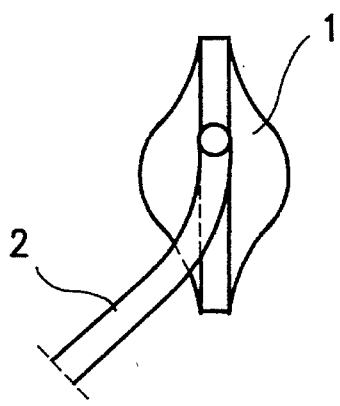
Figure 6:
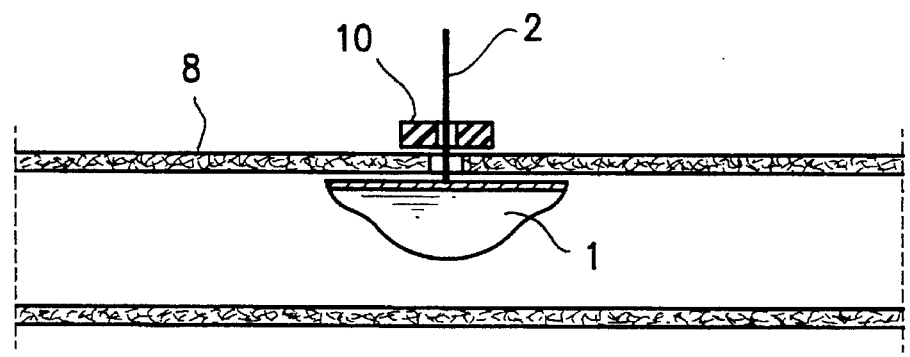
Figure 7:
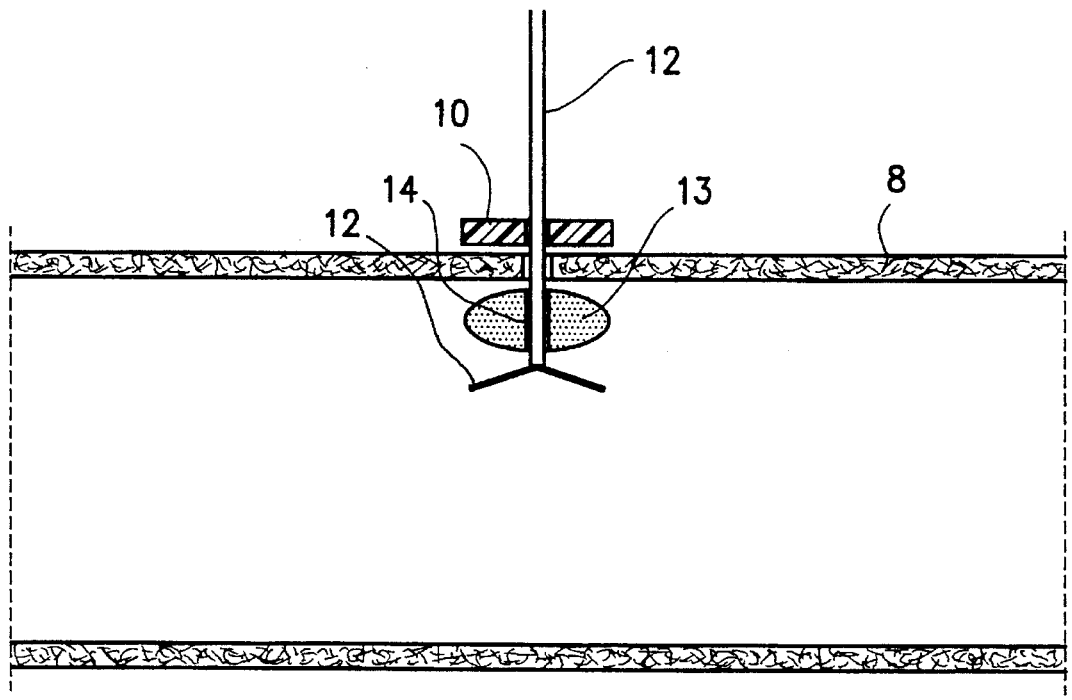

FIG. 5a, b, c show a top view of further embodiments of the occlusion assembly according to the invention;

FIG. 6 shows a further embodiment of the occlusion assembly according to the invention fitted in a blood vessel;

FIG. 7 shows a side view of a further embodiment of the occlusion assembly according to the invention fitted in a blood vessel.

Figure 1:
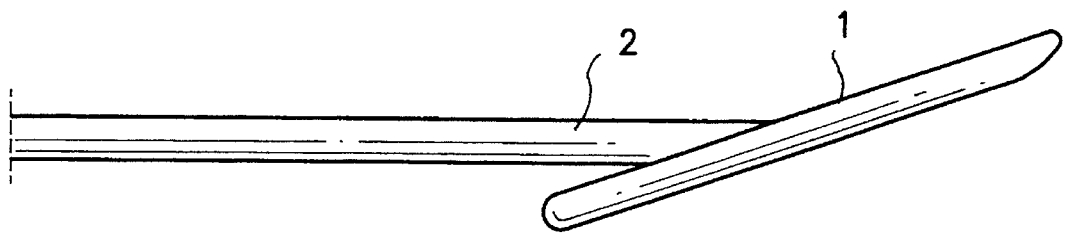
FIG. 1 shows a side view of a first embodiment of the occlusion assembly according to the invention.

A side view of a first embodiment of the occlusion assembly according to the invention is shown in FIG. 1. This comprises a flexible sheet 1 as occlusion element and a retaining element 2, which in this case is in the form of a thread, connected to the centre of said occlusion element. A top view of the various features is drawn in FIG. 2.

Figure 2:
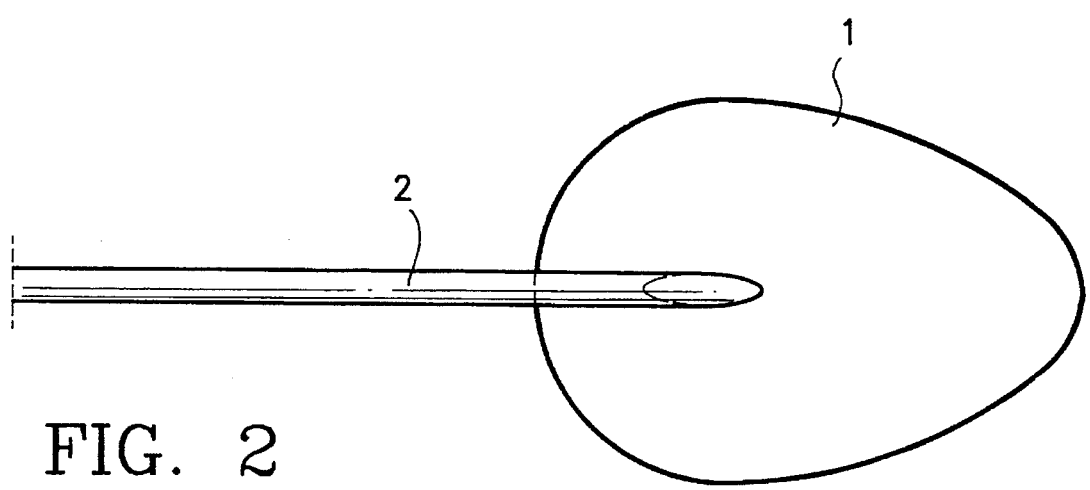
FIG. 2 shows a top view of the same embodiment.
Figure 3:
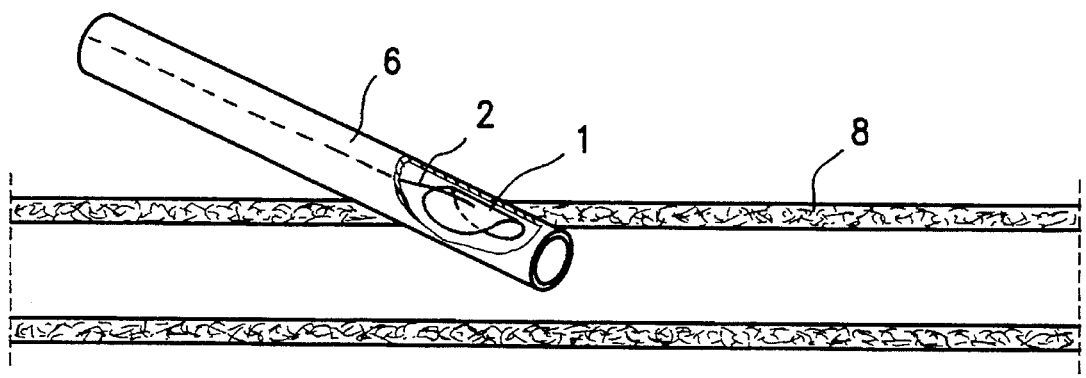
FIG. 3 shows the fitting of the occlusion assembly according to FIG. 1 and 2 in a blood vessel.
Figure 4:
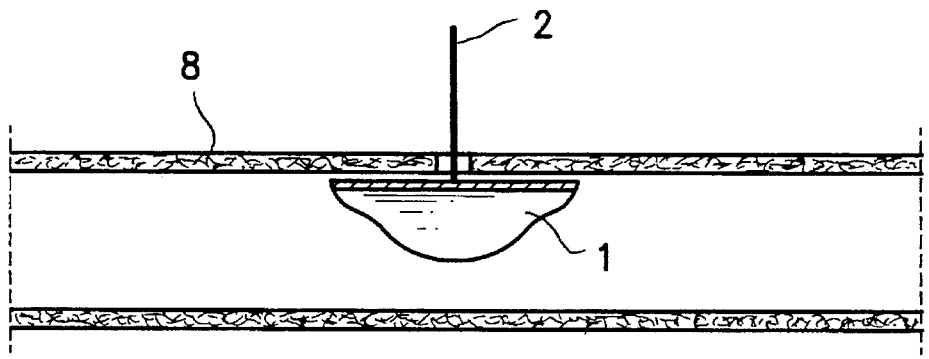
FIG. 4 shows the occlusion assembly according to the above embodiment fitted in a blood vessel.

FIG. B shows a blood vessel 8 in which a sheath 6, known for any medical application, has been inserted. After removing the sheath 6, the problem up to now has been that an appreciable opening was formed in the blood vessel which had to be sealed in some way. The means of sealing described in the prior art were found to be unreliable or to impose restrictions in movement on the patient. According to the invention, the assembly shown in FIG. 1 and 2 is inserted through the sheath, as shown. After the occlusion element 1 has been fitted in the blood vessel 8, the unfoldable sheet 1 unfolds in such a way that the surface area thereof is larger than the surface area of the opening to be occluded. Sheath 6 is then moved out of the opening, as a result of which the latter will become somewhat smaller. By pulling on the retaining thread, sheet 1 will come to lie against blood vessel 8 in the manner shown in FIG. 4. By making both the sheet 1 and retaining element 2 of bioabsorbable material, it is ensured that after the opening in the blood vessel has occluded these parts will disappear, for example after a few weeks.

Various other embodiments of the flexible occlusion element or plug 1 are shown in FIG. 5a, b, c. Depending on the possibilities for insertion through the sheath and the opening made in the blood vessel, these can be used.

A further embodiment of the occlusion assembly according to the invention is shown in FIG. 6. This essentially corresponds to the occlusion assembly described with reference to the above figures except that a retainer ring 10 is fitted over the fixing thread. This retainer ring 10 or locking element serves for accurate determination of the position of occlusion element 1 and is likewise made of a biologically absorbable material. The ring 10 has an internal diameter such that, on the one hand, it can slide in a supple manner over retaining element 2 but, on the other hand, provides some mutual clamping force on these two parts. In contrast to the prior art, the locking element 10 lies against the outside of the blood vessel 8. Consequently, there is tension in the retaining thread only in the part which must bridge the wall thickness of the blood vessel.

A further embodiment of the invention is shown in FIG. 7. The same reference numerals as in the preceding figures have been used for corresponding parts in this figure. In contrast to the earlier embodiments, the retaining thread 2 is now attached to a fixing element 12 which in this case consists of a rod-shaped curved-plated part. The occlusion element, indicated by 13, is provided with an opening 14 located in the centre, through which the retaining element 2 passes. As a result of the use of the fixing element 12, the tension in the retaining thread 2 can be increased, by which means it is guaranteed that the occlusion element 13 remains in its place. With this arrangement, because of the greater strength of the fixing element, pulling of the occlusion element through the opening in the blood vessel is prevented. The fixing element, as well as the occlusion element and the locking element, can be made of a biocompatible material. The occlusion element can contain angiotensin II-converting enzyme inhibitor, an agent which combats constriction of the blood vessels.

It must be understood that the embodiments described above are merely examples and that the invention is not restricted to these. Thus, the fixing element can comprise all means known in the prior art and is not restricted to the thread shown in the drawing. Likewise, the unfoldable element to be inserted in the blood vessel can comprise all possible imaginable configurations.

The invention also relates to the use of bioabsorbable material for the production of an occlusion means for sealing puncture holes in blood vessels, as described above.

The outstanding functioning/characteristics of the occlusion means according to the invention are illustrated with reference to results of in vitro and in vivo tests, which are described below.

IN VITRO TESTS

Aim:
Testing occluder with regard to:

1 strength of fixing thread/plug connection immediately after insertion and after 1 hour
2 pressure resistance of occluder, acute and after 1 hour
3 "blood tightness", acute and after 1 hour
4 effectiveness of occluder in the case of movements
5 effectiveness of occluder for insertion openings of different diameter In order to have a criterion for effectiveness, the occlusion frequency is determined with regard to the insertion frequency (ratio of number of effective occlusions to number of times occluder inserted)

6 unfolding of plug
7 flow pattern of fluid and pressure drop around occluder (turbulence)
8 embolization frequency Test set-up:
All tests are carried out with heparinized fresh blood. The following blood parameters are known:
haemoglobin content (Hb)
haematocrit (Ht)
platelet content
thrombotest (TT)
cephalin time Test set-up for tests 1 to 5 inclusive:
An artery from a test animal (dog, pig) with a diameter of about 7 mm is central in the set-up. This artery is occluded at both ends, on one side by means of a clamp end on the other side by means of a valve. Via this valve the lumen of the artery is connected to a bag of blood which is placed in a pressure bag. The pressure in the blood vessel is kept constant at 150 mm Hg. A sheath with a standard internal diameter of 9 French (2.9 mm) is inserted in the artery by means of the customary technique. The maximum diameter of the plug is standard 4.0 mm.

The insertion module is such that this can be inserted through a standard sheath with an internal cross-section of 5 French (1.65 mm).

The following experiments are carried out in this set-up:
1. Strength of fixing thread/plug connection immediately after insertion end after 1 hour.
   Aim: testing the strength of the fixing thread, the connection between fixing thread and plug and the deformability of the plug under the influence of a force exerted from outside.

Method: this is tested by hanging a weight of 250 gram on the fixing thread for 15 minutes.

2. Pressure resistance of occluder, acute and after 1 hour.
   Aim: testing the mechanical strength end deformability of the plug under the influence of a force from inside.
   Method: this is tested by increasing the pressure in the blood vessel to 300 mm Hg for 15 minutes.

3. "Blood tightness", acute and after 1 hour.
   Aim: testing the amount of blood which passes through the plug and the insertion hole although the plug is mechanically well positioned.
   Method: this measurement is combined with experiment 2. The amount of blood which has diffused through the plug is measured by collecting this blood on dry gauzes and weighing the gauzes before and after the experiment. The difference in weight in grams is regarded as the amount of diffused blood in ml.

4. Effectiveness of occluder in the case of movements.
   Aim: testing the stability of the plug when the blood vessel moves.
   Method: the vessel is fixed at one end and suspended at the other end on an oscillating rod. This rod is moved by an electric motor with a frequency of 1 Hz. A small rod is positioned transversely over the vessel, at about 2 cm from the puncture site, in such a way that said small rod acts as a hinge point for the vessel. The positioning of the vessel is such that the section connected to the rod describes a segment of a circle between 0° and 150°. The puncture site is in the moving part of the vessel. The test time is 30 minutes.

5. Effectiveness of occluder for insertion openings of different diameter.
   Aim: testing the effectiveness of the occluder for insertion openings of different diameter.
   Method: the standard plug with a cross-section of 4 mm is inserted after puncture sites have been made with the following internal sheath diameters: 5 French (1.65 mm), 7 French (2.3 mm) and 9 French (2.9 mm). These tests are carried out under standard conditions and are evaluated using the occlusion/insertion ratio (O/I ratio, 100% success=1, 0% success=0).

Test set-up for tests 6 to 8 inclusive:

An artery originating from a test animal (dog, pig) with a cross-section of about 7 mm is central in the set-up. The set-up further consists of a roller pump, a heat exchanger, a pressure vessel, a haemofilter and a collection vessel. The blood is pumped from the collection vessel (=atmospheric pressure) by the roller pump into the pressure vessel. The pressure vessel is partially filled with air. An adjustable valve, by means of which the fluid can be kept under pressure, is in the top of the pressure vessel. Any air bubbles entrained in the blood pumped from the collection vessel can be removed in the pressure vessel. From the pressure vessel, the blood flows to the artery via a heat exchanger. Two pressure lines (upstream and downstream of the plug) and a temperature measuring point are fitted in the artery. Downstream of the vessel there is a haemofilter and an adjustable resistance. During the experiment the temperature is kept at 37° C. and the pressure upstream of the plug at 150 mm Hg. Flow can be measured after passage of the blood through the haemofilter downstream of the vessel downstream of the resistance, before the blood flows back into the collection vessel, by means of a graduated beaker and a chronometer.

If necessary, the vessel is supported on the outside by a (plastic) tube to simulate the tissue pressure. The position of the insertion opening is left exposed in this case. For evaluation of flow speeds and flow patterns around the plug use can be made of a standard colour Doppler Echo apparatus.

The following experiments are carried out in this set-up:

6. Unfolding of plug.
   Aim: testing to determine whether the plug unfolds as expected.
   Method: it is attempted to visualize the plug by means of echography and to determine the shape.

7. Flow pattern of fluid and pressure drop around occluder (turbulence).
   Aim: testing to establish that the plug does not cause stenoses.
   Method: after initial measurements of pressure and flow, the plug is inserted. After insertion of the plug these measurements are repeated to determine whether the plug has a stenosing action. The flow pattern around the plug is also visualized with the aid of colour Doppler Echo.

8. Embolization frequency.
   Aim: testing to establish that the plug does not act as an embolization source.
   Method: after each insertion of the plug, blood circulated for 2 hours. The haemofilter is then checked and replaced. The pores of the haemofilter are the same size as those of filters used in extracorporal circulation. The number, the size and, where possible, the composition of the emboli are documented.

Tests 6, 7 and 8 can be carried out simultaneously. Tests 6 and 7 are carried out both at the start and just before the end the experiments.

IN VIVO TESTS

In the case of in vivo tests the following points are of importance:

stability of plug haemorrhaging rate at the site of the puncture hole effect of rapid mobilization on stability of the plug vessel recovery at the puncture site formation of aneurysms at the puncture site frequency of stenosis at the site of the plug absorption of plug and fixing thread with time scarring around plug and fixing thread thrombogenicity of plug frequency of embolization of plug material occurrence of infections at the site of the plug toxicity of plug and fixing thread The test animal is an animal of adequate size (dog, pig). After adequate anaesthesia and connection for artificial respiration, a catheter is inserted in the a. carotis for pressure registration. Heparinization is effected by intravenous administration of 100 U/kg of body weight. Blood is taken determine haemoglobin (Hb), haematocrit (Ht), platelets, thrombotest (TT) and cephalin time.

A blood vessel of adequate diameter is sought (a. iliaca, aorta). Via a catheter in the a. carotis, an initial angiogram is made of the blood vessel to be punctured. A standard 9 French sheath is inserted, followed by the insertion of the standard plug (diameter 4 mm).

Depending on the size of the selected blood vessel, one or more puncture sites may be made. After inserting the plug, there is a 15 minute period of observation to determine whether the plug remains stable in place and whether there is any "oozing" at the puncture site (semi-quantitative assessment). After the procedure, a check angiography of the punctured vessel segment is made before removing the sheath from the a. carotis. In the event of survival, blood is taken the following day to determine Hb and Ht. A clinical evaluation is also carried out to determine whether there are any emboli. Before termination, a check angiography is made of the punctured vessel segment. After termination, the puncture site is sought and removed and fixed in formalin (for light microscopy) or glutaraldehyde (for scanning electron microscopy, SEM).

Survival periods in days: 0, 1, 7, 30, 90, 180.

A control group consists of test animals which undergo the same procedure except for the arterial puncture.

The results of both the in vivo and in vitro tests indicate that the occlusion means according to the invention is outstandingly suitable for the intended application.

We claim:

1. An occlusion assembly for percutaneously sealing a puncture in the wall of an artery or vein in the human body comprising:
   a flexible retaining element;
   a pair of clamping members mounted to the retaining element each of said clamping members being sized to be placed entirely beneath the surface of the skin and in turn having a surface for engaging the wall; both of the clamping members being insertable percutaneously below the skin to be engageable with the wall of the artery or vein;
   one of the clamping members being capable of being passed through the puncture in the artery or vein and being constructed to lie in facing contact against the internal surface of the artery or vein adjacent the site of the puncture, the other clamping member being movable along the retaining element toward the first mentioned clamping member to engage and lie in facing contact against the outside surface of the artery or vein thereby to clamp the wall of the artery or vein directly between the two clamping members to prevent blood flow through the puncture sufficiently to enable the puncture to heal;
   at least one of the clamping members being formed from a bioabsorbable material.

2. An occlusion assembly as defined in claim 1 wherein one of the clamping members comprises an occlusion element and the other clamping member comprises a locking element for cooperation with the occlusion element to clamp the wall of the artery or vein therebetween.

3. An occlusion assembly as defined in claim 2 wherein the occlusion element is sized to be passed through the puncture in the artery or vein to engage the inner surface of the artery or vein and the locking element is sized to lie against the outside of the artery or vein.

4. An occlusion assembly as defined in claim 3, wherein the occlusion assembly further comprises a fixing element firmly connected to the retaining element.

5. An occlusion assembly as defined in claim 4 wherein the fixing element comprises a curved rod-shaped element and the retaining element is attached to the center thereof such that when the retaining element is tensioned the center of the rod-shaped element is drawn against the occlusion element.

6. An occlusion assembly as defined in any one of claims 1–5 wherein both of the clamping members are formed from a bioabsorbable material.

7. An occlusion assembly as defined in any one of claims 1–5 further comprising:
   a portion of the flexible retaining element between clamping members, when the wall of the artery or vein is clamped between the two clamping members, is in tension.

8. An occlusion assembly as defined in claim 7 wherein said portion of the retaining element comprises the only portion of the retaining element that is maintained in tension after the artery or vein wall has been clamped.

9. An occlusion assembly as defined in claim 6 wherein the retaining element is formed from a bioabsorbable material.

10. An occlusion assembly as defined in claim 9 wherein the retaining element comprises a thread.

11. An occlusion assembly as defined in claim 1 wherein the retaining element comprises a thread.

12. An occlusion assembly as defined in claim 1 wherein at least one of the clamping members covers fully the puncture.

13. An occlusion assembly as defined in claim 1 further comprising a fixing element attached to the end of the retaining element to provide additional support for said one clamping member and to facilitate urging of the first clamping member firmly against the inner surface of the artery or vein.

14. An occlusion assembly as defined in claim 1 wherein at least one of the occlusion members contains a medicament to promote healing of the puncture site.

15. An occlusion assembly as defined in claim 1 further comprising a tubular member having an end insertable into the artery or vein through the puncture, the tubular member being constructed to receive the clamping members and retaining members to guide them to the region of the puncture.

16. An occlusion assembly for sealing an opening in a wall of blood vessels, comprising a first occlusion component sized for introduction through the opening in the wall of a blood vessel and into engagement with an inner surface of said wall to preclude withdrawal through said opening, a retaining element secured to said first component with a portion of said element passing through said opening with said first component, and a second occlusion component engaging the retaining element, characterized in that the second component is sized to lie beneath the surface of the skin and adjacent the outside of the blood vessel wall with the portion of the retaining element which passes through said opening of the blood vessel between the first component and second component in use being in tension for clamping the wall of the blood vessel therebetween.

17. An occlusion assembly according to claim 16 wherein at least one occlusion component contains a stenosis combatting agent therein.

18. An occlusion assembly according to claim 16 wherein at least one occlusion component contains an agent therein which combats constriction of the wall of the blood vessel.

19. An occlusion assembly according to claim 16 wherein said second component is a locking member sized to be positioned against the outer surface of the wall of the blood vessel.

20. An occlusion assembly according to claim 19 wherein said occlusion assembly further includes a fixing element firmly connected to said retaining element adjacent to said occlusion component to the opposite side thereof from said locking member.

21. An occlusion assembly according to claim 20 wherein said fixing element comprises a curved rod-shaped element.

22. An occlusion assembly according to claim 19, wherein said locking member is movable along the retaining element.

23. An occlusion assembly according to claim 16, wherein said second occlusion component is movable along said retaining element.

24. An occlusion assembly for sealing an incision in the body of a patient wherein the incision extends through the skin of the patient and through a blood vessel wall, defining an opening therein, the assembly comprising;

a bioabsorbable occlusion element;

a bioabsorbable retaining element operatively connected to said occlusion element and extending proximally of said occlusion element in the incision in use; and a bioabsorbable locking element sized to be received beneath the surface of the skin of the patient and in the incision and wherein said locking element is operatively connected to said retaining element to, in cooperation with said occlusion element, obstruct the flow of blood through the incision.

25. The occlusion assembly of claim 24 wherein said locking element is movable along said retaining element.

26. The occlusion assembly of claim 25 wherein said occlusion element is sized to be received through an opening in the blood vessel and generally parallel to said retaining element in a first orientation of said occlusion element.

27. The occlusion assembly of claim 26 wherein said occlusion element is generally perpendicular to said retaining element in a second orientation of said occlusion element.

28. The occlusion assembly of claim 24 wherein said occlusion element is movable along said retaining element and is insertable into said incision in a first orientation.

29. The occlusion assembly of claim 28 wherein said occlusion element is in a second orientation when the incision is sealed from the flow of blood passing through the blood vessel opening and said locking element is operatively connected to said retaining element to fix said occlusion element in said incision.

30. The occlusion assembly of claim 24 wherein a portion of said retaining element between said occlusion element and said locking element is in tension when the incision is sealed from the flow of blood passing through the blood vessel wall opening.

31. The occlusion assembly of claim 24 wherein said locking element engages at least a portion of said retaining element, and said locking element and said occlusion element are in a spaced relationship along said retaining element as the incision is sealed from the flow of blood passing through the blood vessel wall opening.

32. A bioabsorbable occlusion assembly for introduction into an incision and for sealing an opening in the wall of a blood vessel within said incision comprising;

an occlusion element which is sized to be fitted through the opening in the wall of a blood vessel and lie generally adjacent thereto in use;

a retaining element sized for reception in the incision and in operative connection with said occlusion element to extend proximally thereof in the incision; and a locking element sized to be received in the incision and beneath the skin and operatively connected to said retaining element to retain the wall of the blood vessel between said locking element and said occlusion element in use.

33. The occlusion assembly of claim 32 wherein said locking element is movable along said retaining element to a position generally adjacent to the wall of the blood vessel to seal the incision from the flow of blood passing through the blood vessel opening.

34. The occlusion assembly of claim 32 wherein said occlusion assembly includes a stenosis combatting agent combined with at least one of said occlusion element and said locking element.

35. The occlusion assembly of claim 32 wherein said occlusion element is movable between a first orientation during insertion and a second orientation in use.

36. The occlusion assembly of claim 35 wherein said occlusion element is oriented generally parallel to said locking element in said second orientation.

37. The occlusion assembly of claim 32 wherein at least one of said occlusion element and said locking element is movable along said retaining element toward the other of said locking element and said occlusion element.

38. Method for fitting an occlusion assembly in an opening in a blood vessel, comprising the positioning of a sheath through the opening in the blood vessel, guiding an occlusion element and a retaining element, which is coupled therewith, through said sheath into the blood vessel, removing the sheath from the opening in the blood vessel and placing a locking element on the retaining element, characterized in that the locking element is sized to lie beneath the surface of the skin and against the outside of the blood vessel.

39. Method according to claim 38, wherein the retaining element is connected to a fixing element, wherein the method further include inserting the fixing element in the sheath before the occlusion element is guided therethrough.

40. A method for percutaneously sealing a percutaneously formed puncture in the wall of an artery or vein comprising:

providing an occlusion assembly comprising a flexible retaining element and a pair of clamping members mounted to the retaining element, at least one of the clamping members being formed from a bioabsorbable material, both of the clamping members being sized for insertion percutaneously below the surface of the skin to be engageable with the artery or vein, one of the clamping members being sized to be passed through the puncture in the artery or vein and to lie against the internal surface of the wall of the artery or vein adjacent the side of the puncture, the other clamping member being movable along the retaining element toward the first mentioned clamping member and sized to engage and lie against the outside surface of the wall of the artery or vein entirely beneath the surface of the skin thereby to clamp the wall of the artery or vein directly between the two clamping members;

percutaneously inserting the occlusion assembly into the artery or vein by passing the first mentioned of said clamping members through the puncture into the lumen of the artery or vein;

thereafter urging the second mentioned of said clamping members along the retaining element toward and into engagement with the outside surface of said artery or vein entirely beneath the surface of the skin thereby to clamp the wall of the artery or vein directly between the two clamping members sufficiently to seal the puncture in the artery or vein.

41. A method as defined in claim 40 wherein the step of percutaneously inserting the occlusion assembly into the artery or vein further comprises:

providing a tubular member through which the occlusion assembly may be passed;

positioning one end of the tubular member through the puncture in the artery or vein to communicate with the interior of the artery or vein;

advancing the occlusion assembly through the tubular member to cause the first mentioned of the clamping members to pass through the puncture into the lumen of the artery or vein;

after the first clamping member has been disposed within the artery or vein, withdrawing the tubular member from the artery and locating the end of the tubular member in proximity to the outer surface of the artery or vein;

thereafter advancing the other clamping member through the tubular member and along the retaining member to cause the other clamping member to engage the outer surface of the artery or vein; and removing the tubular member from within the patient.

42. A method as defined in claim 41 wherein the step of advancing the second clamping member into engagement with the outer surface of the artery or vein comprises urging the second clamping member toward the first clamping member along the retaining member sufficiently to develop a tension in that portion of the retaining member that extends between the clamping members.

43. A method as defined in any one of claims 40–42 further comprising:

maintaining the clamping members in said clamping engagement with the wall of the artery or vein for a sufficient length of time to enable the puncture to become biologically occluded.

44. A method as defined in any one of claims 40–42 further comprising:

applying a medicament to the wall of the artery or vein in the region of the puncture.

45. A method as defined in claim 44 wherein the applying of the medicament comprises incorporating the medicament into one of the clamping members.

46. A method as defined in claim 44 wherein the medicament comprises angiotensin II-coverting enzyme inhibitor.

47. A method of inserting an occlusion assembly contained within a sheath member into an incision to seal an incision that extends through the skin of a patient and through the wall of a blood vessel, said occlusion assembly including a sheath member with an occlusion element and a retaining element positioned in the sheath, and a locking element, said occlusion element and locking element being sized to be placed entirely beneath the surface of the skin within the incision, the method including;

positioning the sheath member through the incision and past the wall of the blood vessel, retracting said sheath and retaining the occlusion element within the blood vessel, and positioning the locking element in the incision beneath the surface of the skin, moving at least one of the locking element and the occlusion element toward the other along the retaining element and beneath the surface of the skin wherein the locking element is spaced apart from the occlusion element to stabilize the occlusion element and seal the incision from the flow of blood therethrough.

48. The method of claim 47 further including adjusting the occlusion element during insertion so that the occlusion element is oriented generally parallel to the wall of the blood vessel.

49. The method of claim 47 further including moving the locking element along the retaining element to a fixed position in the incision along the retaining element.

50. The method of claim 47 further including positioning the locking element in the incision along the retaining element to securely hold the occlusion element along the wall of the blood vessel and tensioning the retaining element between the locking element and the occlusion element.

51. A method of inserting an occlusion assembly comprising an occlusion element, a locking element and a retaining element into an incision to seal an incision that extends through the skin of a patient and into a blood vessel, said occlusion assembly being sized to be placed beneath the surface of the skin in the incision, the method comprising the steps of:

inserting the occlusion assembly into the incision and blood vessel; and moving at least one of said locking element and said occlusion element toward the other of the locking element and the occlusion element to a position in the incision and blood vessel wherein the locking element is spaced apart from the occlusion element and positioned below the surface of the skin in the incision to occlude a portion of said incision and the flow of blood through the incision from the blood vessel.

52. The method of claim 51 wherein the occlusion element is moved from a non-occluding orientation during insertion to an occluding orientation along the wall of the blood vessel.

53. The method of claim 51 further including positioning the locking element in a fixed relationship along the retaining element.

54. The method of claim 51 further including orienting the occlusion element generally parallel to the retaining element during insertion and generally perpendicular thereto as the occlusion element is positioned along the wall of the blood vessel.

55. The method of claim 54 further including compressing the occlusion element after insertion to be oriented generally parallel to the wall of the blood vessel.

56. The method of claim 51 further including placing the portion of the retaining element between the occlusion element and the locking member in tension when the occlusion element is positioned along the wall of the blood vessel.

57. The method of claim 51 further including compressing the occlusion element after insertion to be oriented generally parallel to the wall of the blood vessel.

58. The method of claim 51 further including positioning of the locking element in the incision along the retaining element to securely hold the occlusion element along the wall of the blood vessel.

59. The method of claim 51 further including positioning of the locking element in the incision and tensioning the retaining element between the locking element and the occlusion element.

60. A method of inserting an occlusion assembly comprising an occlusion element, a locking element and a retaining element into an incision to seal an incision that extends through the skin of a patient and into a blood vessel, the method including the steps of:

inserting the occlusion assembly into the incision and below the surface of the skin; and positioning a bioabsorbable locking element in the incision between beneath the surface of the skin of a patient and the blood vessel to obstruct the flow of blood through the incision from the blood vessel of the patient.

61. The method of claim 60 further including the step of positioning an occlusion element in the blood vessel generally adjacent to the incision such that the occlusion element and the locking element cooperatively obstruct the flow of blood through the incision from the blood vessel.

62. The method of claim 61 further including the step of moving the bioabsorbable locking element along a retaining element in the incision to obstruct the flow of blood through the incision from the blood vessel of the patient.

63. The method of claim 62 further including the step of tensioning said retaining element between the locking element and the occlusion element in the incision.

64. The method of claim 60 wherein positioning the bioabsorbable locking element includes the step of moving the bioabsorbable locking element along a retaining element in the incision to a location generally between the skin of the patient and the blood vessel.

65. A method for fitting a bioabsorbable occlusion assembly in an opening in a blood vessel, said occlusion assembly including a sheath with a bioabsorbable occlusion member and a bioabsorbable retaining element received in said sheath, said assembly further including a locking element, said occlusion element and locking element being sized to be placed entirely beneath the surface of the skin within the incision, said method comprising;

positioning the sheath through the opening in the blood vessel;

guiding the occlusion member and the retaining element through the sheath and into the blood vessel;

retracting said sheath and retaining the occlusion element within the blood vessel, and positioning the locking element in the incision beneath the surface of the skin, and moving the occlusion member and the locking element and the retaining element relative to said sheath to engage over said opening in the blood vessel and obstruct the flow of fluids through the opening.

66. The method of claim 65 including the step of causing movement of the occlusion member from a first position to a second position wherein the occlusion member is generally aligned along the wall of the blood vessel.

67. The method of claim 66 including the step of moving the locking element along the retaining element toward the occlusion member upon engagement over said opening.

68. The method of claim 65 including the further step of tensioning the portion of the retaining element between the locking element and the occlusion member.

* * * * *

UNITED STATES PATENT AND TRADEMARK OFFICE
CERTIFICATE OF CORRECTION

PATENT NO. : 5,593,422

DATED : January 14, 1997

INVENTOR(S) : Muijs Van de Moer et al

It is certified that error appears in the above-indentified patent and that said Letters Patent is hereby corrected as shown below:

On the title page, item [63] Related U. S. Application Data, "PCT/NL90/00078, May 29, 1989" should read --PCT/NL90/00078, May 29, 1990--.

Signed and Sealed this

First Day of April, 1997

Attest:

BRUCE LEHMAN

*Attesting Officer*   *Commissioner of Patents and Trademarks*